United States Patent [19]

Bein et al.

[11] Patent Number: 5,151,110
[45] Date of Patent: Sep. 29, 1992

[54] MOLECULAR SIEVE SENSORS FOR SELECTIVE DETECTION AT THE NANOGRAM LEVEL

[75] Inventors: Thomas Bein; Kelly D. Brown; Gregory C. Frye; Charles J. Brinker, all of Albuquerque, N. Mex.

[73] Assignee: University of New Mexico, Albuquerque, N. Mex.

[21] Appl. No.: 580,373

[22] Filed: Sep. 11, 1990

[51] Int. Cl.$^5$ ............................................. B01D 53/04
[52] U.S. Cl. ....................................... 55/75; 55/67; 55/208; 55/386; 55/389
[58] Field of Search ................. 55/208, 270, 274, 389, 55/197, 386, 18–21, 74, 75

[56] References Cited

U.S. PATENT DOCUMENTS

| | | | |
|---|---|---|---|
| 3,164,004 | 1/1965 | King | 73/23 |
| 3,309,844 | 3/1967 | Hemstreet et al. | 55/389 X |
| 3,372,531 | 3/1968 | Hoenig | 55/389 X |
| 4,208,194 | 6/1980 | Nelson | 55/389 X |
| 4,244,713 | 1/1981 | Goodwin | 55/270 X |
| 4,595,403 | 6/1986 | Sago et al. | 55/389 |
| 4,599,095 | 7/1986 | Barnes et al. | 55/208 |
| 4,865,996 | 9/1989 | Castleman et al. | 55/208 X |
| 4,925,459 | 5/1990 | Rojey et al. | 55/389 X |
| 4,935,040 | 6/1990 | Goedert | 55/208 X |
| 4,936,877 | 6/1990 | Hultquist et al. | 55/270 X |

OTHER PUBLICATIONS

Bein et al., "Molecular Sieve Sensors for Selective Detection at the Nanogram Level," Journal of the American Chemical Society, vol. 111, No. 19, pp. 7640–7641, Sep. 13, 1989.
Lynch (editor), *CRC Handbook of Materials Science*, vol. 111, Nonmetallic Materials and Applications, CRC Press, Inc.: Boca Raton, FL, pp. 198–200 (1975).
Ku et al., *Electrical Properties of Polymers*, Hanser Publishers, Munich, pp. 7–17 (1987).
Ricco et al., "Determination of BET Surface Areas of Porous Thin Films Using Surface Acoustic Wave Devices," Langmuir, 5, pp. 273–276 (1989).
Brinker et al., ed., "Better Ceramics Through Chemistry 111", Mat. Res. Soc. Symp. Proc., vol. 121, Materials Research Soc., pp. v–xiii Apr. 5–8, 1988.
Carey et al., "Multicomponent Analysis Using an Array of Piezoelectric Crystal Sensors," Analytical Chem., vol. 59, pp. 1529–1534 (1987).
Carey et al., "Monitoring a Dryer Operation Using An Array of Piezoelectric Crystals", Analytical Chem. vol. 60, pp. 541–544 (1988).
Frye et al., "Characterization of the Surface Area and Porosity of Sol-Gel Films Using SAW Devices", Mat. Res. Soc. Symp. Proc., vol. 121, Materials Research Company, pp. 349–354 (1988).
J. Am. Chem. Soc., 111, pp. 7640–7641 (1989).
C&EN, Sep. 25, 1989, p. 32.
MRS Bulletin, May 1990, pp. 10–11.
Chemecology, vol. 19, No. 2, Mar. 1990, p. 5.
C&EN, Jan. 29, 1990, pp. 24–26.
"Advances in Sensor Technology Promise Reduce Risk From Toxic Substrates", News Release, Materials Research Society, pp. 1–5 (Apr. 1990).
Inside R&D, vol. 19, No. 16, Apr. 18, 1990.
Browne, "Gains Reported in Detecting Toxic Substances", The New York Times Science, Dec. 26, 1989.

*Primary Examiner*—Robert Spitzer
*Attorney, Agent, or Firm*—Millen, White & Zelano

[57] ABSTRACT

The invention relates to a selective chemical sensor for selective detection of chemical entities even at the nanogram level. The invention further relates to methods of using the sensor. The sensor comprises:

(a) a piezoelectric substrate capable of detecting mass changes resulting from adsorption of material thereon; and (b) a coating applied to the substrate, which selectively sorbs chemical entities of a size smaller than a preselected magnitude.

12 Claims, 1 Drawing Sheet

MOLECULAR SIEVE SENSORS FOR SELECTIVE DETECTION AT THE NANOGRAM LEVEL

The U.S. government has rights in this invention pursuant to Contract No. DE-AC-04-76DPO0789.

BACKGROUND OF THE INVENTION

Determining and/or monitoring the presence of certain chemical species within an environment, e.g., pollutants, toxic substances, and other undesirable compounds, is becoming of increasing importance with respect to such fields as health, environmental protection and resource conservation.

There exists very sophisticated and complicated systems which are capable of detecting the presence of, for example, a substance in the atmosphere, even down to as low a level as a trillionth of a gram. However, many devices are impractical for field applications. For example, in analyzing water or soil samples for the presence of harmful substances, the samples are generally collected from the field and then taken to the lab and subjected to analysis using, for example, a gas chromatograph and/or a mass spectrometer. These types of analysis equipment, while very sophisticated and precise, are not practical for use in the field, require a substantial capital investment, and often take a long period of time for completion of analysis, i.e., often up to several days.

There are devices which are less expensive and smaller in size than those discussed above which provide for a detection of a change in mass. These devices are known as piezoelectric sensors, such as surface acoustic wave (SAW) or quartz crystal microbalance (QCM) devices. They are based on a piezoelectric crystal. By employing an alternating voltage to an interdigital transducer on the piezoelectric crystal, there results a surface acoustic wave. The propagation velocity of this surface acoustic wave is a sensitive probe of near surface mass changes and elastic moduli. Thus, when a substance adsorbs onto the surface of the SAW devices, there is produced a response. SAW devices are capable of detecting mass changes as low as about 100 pg/cm$^2$. Similarly, an alternating voltage at the two opposite electrodes on a QCM (AT-cut quartz) induces a thickness shear mode whose resonance frequence is proportional to mass. However, while these devices are very sensitive mass detectors, they are not inherently selective with respect to different substances.

SUMMARY OF THE INVENTION

An object of the invention, therefore, is to provide a sensitive and selective chemical sensor and methods of using the same, wherein the sensor is both inexpensive to produce and suitable for field applications. Furthermore, the sensor preferably provides a short time analysis and is capable of selective detection of substances at the nanogram level.

Upon further study of the specification and appended claims, further objects and advantages of this invention will become apparent to those skilled in the art.

These objects are achieved by providing an article of manufacture comprising:

(a) a piezoelectric substrate; and (b) a coating applied to the substrate which selectively sorbs chemical entities of a size less than a preselected magnitude.

These objects have also been achieved by providing a chemical sensor comprising:

(a) a piezoelectric substrate capable of detecting mass changes resulting from adsorption of material; and (b) a coating applied to the substrate, which selectively sorbs chemical entities of a size less than a preselected magnitude.

In addition, according to a method aspect of the invention, there is provided a method for selectively detecting the presence of a chemical entity within an environment comprising placing a selective chemical sensor as described above in the environment and detecting the mass changes of sorption of material onto piezoelectric substrate/coating composite.

By "selective sorption" is meant that only chemical entities of a certain size will be sorbed. For example, only chemical entities of a certain maximum size will be capable of entering the pores within the coating or film and in some manner (adsorption, absorption, entrapment, etc.) retained so that the overall mass of the piezoelectric substrate/coating composite increases.

The term "chemical entities" refers to atoms and molecules.

Regarding the piezoelectric substrate, the substrates used in accordance with the invention are those known in the art, for example, ST-cut quartz. In addition to quartz crystals, piezoelectric ceramics such as those of the barium titanate and lead titanate zirconate families are suitable substrates. These include LiNbO$_3$, BaTiO$_3$, 95 wt. % BaTiO$_3$/5% CaTiO$_3$, 80 wt. % BaTiO$_3$/12% PbTiO$_3$/8% CaTiO$_3$, PbNb$_2$O$_6$, Na$_{0.5}$K$_{0.5}$NbO$_3$, Pb$_{0.94}$Sr$_{0.06}$(Ti$_{0.48}$Sr$_{0.52}$)O$_3$, and Pb(Ti$_{0.48}$Sr$_{0.52}$)O$_3$.

The piezoelectric properties of these and other suitable material are provided in "CRC Handbook of Materials Science", Volume III, Charles T. Lynch, CRC Press: Boca Raton, Fla. pp. 198, (1975). For more information regarding piezoelectric materials see Jaffe, B.; Cook, W. R.; Jaffe, H., "Piezoelectric Ceramics", Academic Press, New York (1971).

Fluoropolymers such as poly(vinylidene)difluoride and related copolymers are another family of appropriate piezoelectric substrates. See Ku, C. C.; Liepins, R., "Electrical Properties of Polymers", Hanser Publishers; Munich, pp. 7 (1987).

The piezoelectric substrate is preferably contained within a SAW device or QCM device. The former device comprises a source of alternating voltage which is applied to an interdigital transducer. The interdigital transducer is located on the piezoelectric substrate and, through the application of the alternating voltage induces, the formation of a surface acoustic wave on the substrate. Changes in the propagation velocity or resonance frequence, provide for the detection of mass changes resulting from substances adsorbing into a film on the piezoelectric crystal.

If the SAW device is operated as the frequency control element in an oscillator circuit, relative changes in frequency $\Delta f/f_o$ reflect perturbations in acoustic wave velocity, $\Delta v/v_o$. When mass loading is the dominant perturbation to the SAW, frequency changes can be related to mass loading by $$\Delta f/f_o = k\Delta v/v_o = -kc_m f_o mn,$$

wherein k is the fraction of the path length between the transducers covered by an adsorbing film, c is the mass sensitivity of the device (e.g., $1.3 \times 10^{-6}$ cm$^2$−s/g for an ST-cut quartz crystal), and n and m are respectively the number density and mass of the adsorbed molecules.

For example, the frequency stability of a device (about 1 Hz/min. under ideal conditions) operated at 97 MHz results in detection limits on the order of 100 pg/cm$^2$. For a further discussion on SAW devices, see "Characterization of the Surface Area and Porosity of Sol-Gel Films using SAW Devices", Frye, G., et al., Mat. Res. Soc. Symp. Proc., Materials Research Co., Pittsburgh, Vol. 121, 349 (1988) and "BET Surface Areas of Porous Thin Films Using Surface Acoustic Wave Devices", Ricco et al., Langmuir, 5, 273 (1989).

The thin film which provides the selectivity for the sensor exhibits molecular sieving properties. In this sense, the thin film, for example, permits the passage into its pores of chemical entities having a certain maximum effective diameter while excluding the passage of all chemical entities having an effective diameter larger than that maximum effective diameter. The molecules to be detected pass into the pores within the thin film and are sorbed. Their presence within the composite induces a mass change which is detected at the same time.

The molecular sieving properties of the thin film are preferably provided by the presence of zeolite crystals. Zeolites are natural or synthetic porous crystalline structures. Zeolite crystals, e.g., zeolite Y, zeolite X, zeolite A, ZSM-5, etc., are typically made of silicon, aluminum and oxygen. For a general discussion of zeolite structures, see Meier, W. M.; Olson, D. H., "Atlas of Zeolite Structure Types", 2nd Edition, Butterworths: London, 1987. This atlas contains the structures and pore diameters of about 70 zeolite types. Table I provides an exemplary list of suitable zeolites.

TABLE I

| | Main pore diameter (Å) | Dimensionality |
|---|---|---|
| AlPO$_4$-5 | 7.3 | * |
| Chabazite | 3.8 | *** |
| Erionite | 3.6 × 5.1 | *** |
| Faujasite | 7.4 | *** |
| Gmelinite | 7.0 | * |
| Linde A | 4.1 | *** |
| Linde L | 7.1 | * |
| Mazzite | 7.4 | * |
| ZSM-5 | 5.3 × 5.6/5.1 × 5.5 | *** |
| Mordenite | 6.5 × 7.0 | * |
| Offretite | 6.7 | * |
| Rho | 3.6 | *** |

The dimensionality of the channel system is given as number of *. Some zeolite structures have intersecting smaller channels that might modify the sorption behavior for certain molecules.

Zeolites exhibit substantially uniform pore diameters within their continuous pore systems. These pore diameters are generally about 2.5–12Å. On a microscopic level, the pores within the zeolite structures generally range from a pore defined by a ring of six alternating metal/oxygens atoms up to pores defined by 18 alternating metal/oxygen atoms.

A chemical entity, e.g., a molecule, having an effective diameter smaller than that of the pore diameter of the zeolite crystalline structure will be absorbed in the thin film on the surface of the piezoelectric substrate.

In addition, it is also possible to chemically modify the pores of the zeolite to enhance sorption of chemical entities or to enhance the selectivity of the pores. Such chemical modifications include:

(a) acid/base modifications, and (b) intrazeolite ligation.

In an acid/base modification, the zeolite pore interior is modified such that it becomes Lewis or Bronsted acidic or basic. This causes the corresponding base or acid to be strongly adsorbed. By adjusting the sorption conditions (partial pressure, temperature), a substantial selectivity discrimination against non-acidic/basic molecules such as hydrocarbons is achieved.

For example, the zeolite can be ion-exchanged with NH$_4$Cl in an aqueous solution (before or after deposition as a thin film). After calcination, the zeolite is present in its proton form which is highly acidic. Adsorption of organic amines such as trimethyl amine, other trialkyl amines, pyridine, and others is strong the corresponding ammonium ion is formed. The adsorption is reversible at about 150°–250° C. By raising the sensor temperature, non-polar molecules will not adsorb even though they fit into the zeolite pores.

Related modifications include, e.g., making the zeolite interior basic by adsorbing NaN$_3$/ethanol and subsequent calcination of the zeolite. The zeolite will now be selective for acid vapors such as acetic acid, formic acid, etc. Preferably, high-silica zeolites are used for this embodiment because acid vapors can destroy low-silica zeolites.

Intrazeolite ligation can be used in a manner similar to the acid/base modification. Metal ions are introduced by ion exchange, such as Cu(II) or Rh(III), and the zeolite film is dehydrated at elevated temperature. Certain molecules attach to the metal ions as ligands and are held much stronger than non-ligating molecules. Examples include pyridine or ammonia in a Cu-zeolite, and carbon monoxide in a Rh-zeolite. The entire coordination chemistry of transition metal ions with volatile ligands (as detailed, for example, in Cotton, F. A.; Wilkinson, G., "Advanced Inorganic Chemistry", Fifth Edition, Wiley, New York, 1988), could be introduced into the zeolite pores and utilized for sensor purposes.

The film, with its molecular sieving properties is preferably an inorganic matrix, especially one derived from a sol-gel process. Preferably the matrix is made of silica, e.g., an amorphous SiO$_2$ matrix.

In addition to silica, almost all other sol-gel-derived metal oxides and other materials that form thin films are suitable as matrix materials, including alumina (from, e.g., Al-sec-butoxide), boro-aluminosilicate (from Al-sec-butoxide, TEOS, and trimethyl borate), or titania from Ti tetraisopropoxide. Many examples of sol-gel derived metal oxides and non-oxides are given in "Better Ceramics Through Chemistry III", C. J. Brinker; D. E. Clark; D. R. Ulrich, Editors, Mat. Res. Soc. Symp. Proc.; Materials Research Soc.; Pittsburgh, Vol. 121 (1988).

The different matrices can have different porosity, which determines the adsorption response rate and maximum film thickness. They also can have different environmental stabilities.

The film generally has a thickness of about 0.001–10 μm, preferably 0.01–5 μm, especially about 0.1–1.0 μm. It is difficult, using the sol-gel process, to obtain crack-free films having a thickness above about 10 μm.

Other matrix examples include organically modified sol-gel derived materials, e.g., hydrolyzed diethoxydiphenylsilane, and siloxane rubbers such as poly(dimethylsiloxane)(methylvinylsiloxane) copolymers. The latter have the additional feature that they can be simply dissolved in polar solvents such as ethyl acetate which can provide a deposition technique. However, the resultant films are generally less durable. Zeolite/clay suspensions form other inexpensive matrices which are thermostable.

Finally, zeolites can also be attached to the sensor surface through "anchoring agents" such as gold surface-bound alkoxysilanes (by using alkoxythiols, e.g., $HS(CH_2)_3Si(OCH_3)_3$ that are anchored to the sensor gold electrode through the thiol function and attach to the zeolite through the hydrolyzed alkoxysilane groups). Also, tetraethylorthosilicate (TEOS) can be vapor-deposited on the gold electrode, partially hydrolyzed, and form a "sticky" surface that binds zeolite crystals from a stirred suspension. After heating these systems to about 200° C., the zeolite crystals on the surface even withstand low power sonication. An advantage of the latter deposition is that the zeolite pores will not be clogged with matrix material. Clogging can sometimes be a problem with other matrices and accordingly will reduce the accessible zeolite pore volume.

Preferably, the films are designed as single layers of zeolites protruding from an amorphous $SiO_2$ matrix. The films are made by first providing suspensions of small zeolite crystals having pore sizes of about 0.25–1.2 nm (e.g., about 0.3–0.8 nm, 0.3–0.6 nm, or 0.25–0.45 nm), for example, in an alcoholic solution of a silicon compound such as alkylated silicates, for example, tetraalkylorthosilicates (e.g., TEOS). The suspension is then applied as a film layer to the surface of a piezoelectric substrate resulting in the formation of a thin film microcomposite coating containing protruding zeolite crystals. The substrates can be coated with the films using a variety of conventional application procedures, including dip-coating, painting, spraying, or spin-coating.

For example, zeolite-silica composites can be prepared by suspending small zeolite crystals in an alcoholic solution of tetraethylorthosilicate (TEOS) that is hydrolyzed by acid or base catalyzed reaction and polymerized by condensation resulting in Si—O—Si bonding Inorganic polymer growth can be biased toward extended, weakly branched structures under acid catalyzed conditions, or outward compact, fully polymerized colloidal particles under base catalyzed conditions.

During deposition of the zeolite/silicate suspensions by dip-coating, the solvent is evaporated, concentrating the inorganic components on the substrate surface. Continued polymerization causes the silicate film to gel, "freezing-in" a particular topological configuration and orientation of the incorporated zeolite crystals. Final consolidation of the porous matrix structure to a nonporous, "glass-like" film occurs by further condensation and viscous sintering. After consolidation, impermeable matrices force diffusion through zeolite channels exclusively, while porous matrices allow absorption in zeolite multilayers.

The chemical sensor is suitable for selective detection of a variety of compounds, polar and non-polar. Generally, the sensor can detect any compound having an effective diameter of 0.25–1.2 nm. For example, the sensor can be employed to detect aliphatic hydrocarbons (e.g., methane, butanes, pentanes, hexanes, iso- and n-octane, etc.), aromatics (e.g., benzene, toluene, xylenes, etc.), chlorinated hydrocarbons (e.g., methylene chloride, chloroform, carbon tetrachloride), alcohols (e.g., methanol, ethanol, 1-butanol, etc.), aliphatic amines, aromatic amines, carbon monoxide and water.

The following documents further provide descriptions of embodiments of the invention: J. Am. Chem. Soc., 111, pp. 7640–41 (1989); C&EN, Sept. 25, 1989, p. 32; MRS Bulletin, May 1990, pp. 10–11; Chemecology, Vol. 19, No. 2, March 1990, P. 5; C&EN, Jan. 29, 1990, pp. 24–26; "Advances in Sensor Technology Promise Reduced Risk From Toxic Substrates", News Release, Materials Research Society, pp. 1–5 (April 1990); Inside R&D, Vol. 19, No. 16, Apr. 18, 1990.

The invention also encompasses embodiments comprising two or more of the above-described selective chemical sensors. For example, two sensors used in conjunction could establish a range, with both preselected lower and upper limits, for the effective diameter of the chemical entities to be detected.

For example, in detecting a molecule with an effective diameter of, e.g., 0.5 nm, there can be used two sensors, a first sensor having zeolite crystals with a pore diameter of 0.45 nm and a second sensor having zeolite crystals with a pore diameter of 0.55 nm. If only the second sensor detects a chemical entity, then the effective diameter of the entity will be 0.45 to 0.55 nm. If only the first sensor detects a chemical entity, then the effective diameter of the entity will be $\leq 0.45$ nm. Neither sensor will detect chemical entities with an effective diameter $>0.55$ nm.

Furthermore, a plurality of the sensors could be used in a sensor array, with, e.g., associated control devices and software, in a manner similar to the conventional procedures employed with sensor arrays. See, e.g., W. Patrick Carey, Kenneth R. Beebe, and Bruce R. Kowalski, "Multicomponent Analysis Using an Array of Piezoelectric Crystal Sensors", Analytical Chem., Vol. 59, p. 1529–34 (1987). See, also, Analytical Chem., Vol. 60, 541–544 (1988).

In addition, the sensor could also be used as a detector after chromotographic separation of fluid samples. The small size and low energy consumption of the inventive detector would also permit construction of chromotographs for field use, e.g., in environmental or process monitoring.

Without further elaboration, it is believed that one skilled in the art can, using the preceding description, utilize the present invention to its fullest extent. The following preferred specific embodiments are, therefore, be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application, are hereby incorporated by reference.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF DRAWINGS

Figure 1A:
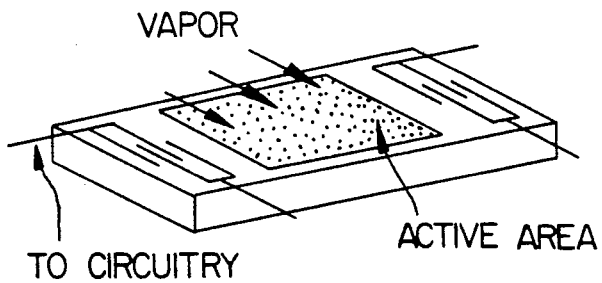
FIG. 1A is a schematic view of a SAW device illustrating the active area which constitutes the sensor.

FIG. 1A shows a surface acoustic wave device in which a portion of the piezoelectric surface is provided with silica matrix-containing zeolites, i.e., the "active area".

Figure 1B:
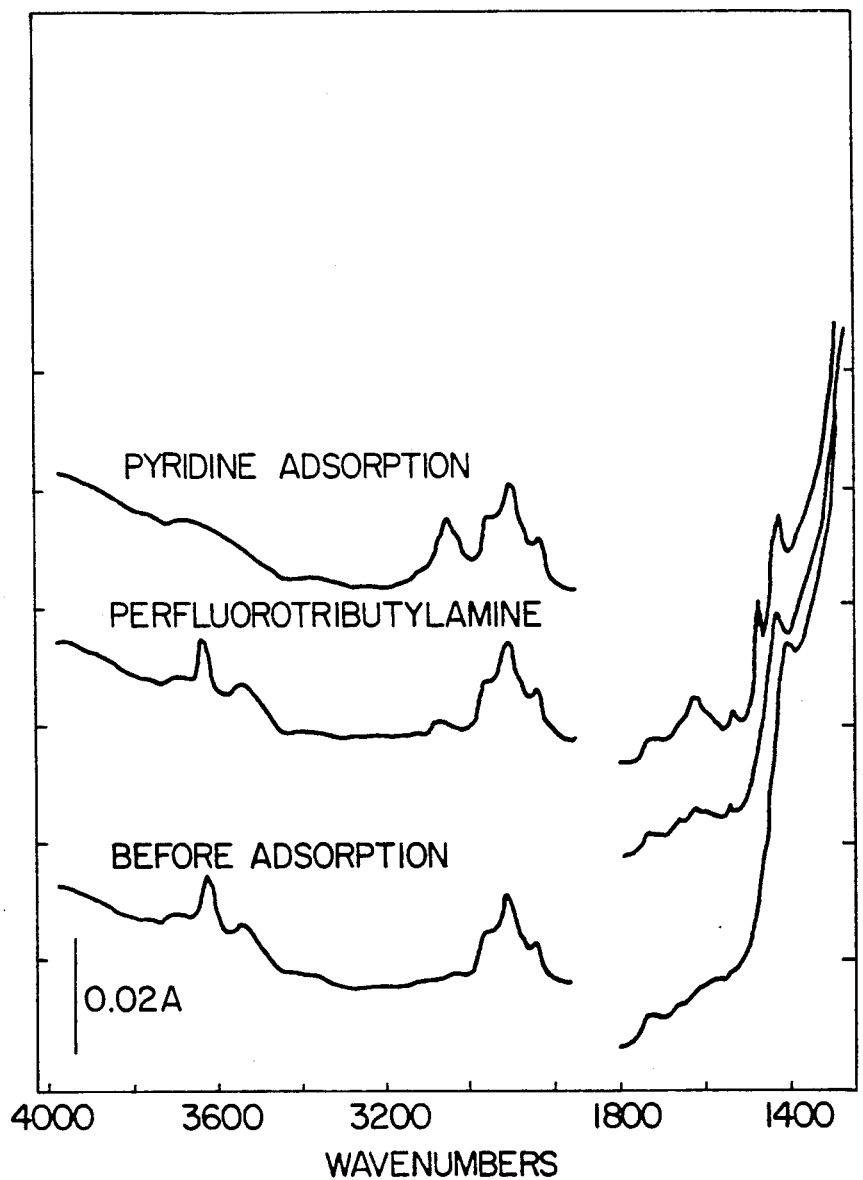
FIG. 1B illustrates adsorption data for pyridine and perfluorotributylamine vapors.

FIG. 1B shows data for adsorption of pyridine and perfluorotributylamine vapor (1 Torr at 295 K) on HY-zeolite film embedded in silica matrix derived from base-catalyzed sol (B2), degassed at 570K, $10^{-7}$ Torr. FTIR spectra were taken at 8 cm$^{-1}$ resolution in a stainless steel UHV cell, equipped with CaF$_2$ windows and connected to a steel apparatus with turbomolecular pump and mass spectrometer. The features in the C—H stretch region (about 2800–3000 cm$^{-1}$) are due to decomposition products the sol matrix deposited on the cell windows after initial heating.

EXAMPLES

EXAMPLE 1

Fabrication of a Sensor with a Zeolite-Sol Composition Coating

1. Synthesis of the Sol STOCK solution:

In a reaction flask equipped with a condensor, thermometer, and a dropping funnel, 1220 ml EtOH+1220 ml tetraethylorthosilicate are added. The mixture is brought to 60° C., and a solution of 4 ml 1M HCl+96 ml deionized water is added dropwise. The resultant mixture is stirred for 1.5 hours at 60° C., and then refrigerated as the STOCK solution.

2. Synthesis of A2 or B2 sols:

A2: to 10 ml of the STOCK solution 0.04 ml water+0.12 ml of 1M HCl are added; the resultant mixture is shaken and refrigerated.

B2: to 10 ml of the STOCK solution 0.05 ml of 1M NH$_4$OH are added; the resultant mixture is shaken and refrigerated.

3. Mixing of the Sol-Zeolite composite, "A" solution: "A" solution of Zeolite+Sol+Solvent are mixed:
i. 3.21 g Zeolite Y +9.63 ml EtOH.
ii. mixture is sonicated for 3 minutes medium power.
iii. solution is allowed to cool to near room temperature, it is shaken to redistribute the suspension, then 2.12 ml sol are added, this is shaken briefly to mix the sol with the suspension.

4. Dip substrates a. Within typically 0–12 hrs, preferably 0–4 hrs, after mixing (step 3), the substrates are dipped in "A" solution, and withdrawn typically at a rate of about 2 inches/min. The withdrawing rate will effect thickness.

b. The coated substrates are placed in an oven for 10 minutes at about 90°–150° C. to "set" coating.

c. Substrates are quick fired for about 5 minutes at about 400° C. in air to eliminate organics in the coating and promote further condensation and consolidation of matrix porosity (if any).

EXAMPLE 2

As demonstrated in Table II, the molecular sieving behavior of zeolite Y (Y, crystal size: 0.2 μm, pore size; 7.5Å), chabazite (CHA, crystal size: 1–3 μm, pore size: 3.7Å), ZMS-5 (crystal size: 0.5 μm, pore size: 5.4×5.6Å) and zeolite A (LTA, crystal size: 3 μm, pore size: 4.1Å) crystals is maintained when they are embedded in TEOS sol-gel derived glassy thin films. For example, the acid form of zeolite Y embedded in a silicate-based film adsorbs pyridine (5.9Å effective diameter) as shown by consumption of the intrazeolite bridged hydroxyl groups (at 3540 and 3640 cm$^{-1}$) and the formation of pyridinium ions (band at 1545 cm$^{-1}$; FIG. 1B). However, exposure of a similar film to pertrifluorobutylamine (10.2Å) does not indicate any reaction with the internal bridged hydroxyls. Similarly, acidic chabazite-based films (pore size 3.7Å) react with ammonia (2.6Å) but not with tributylamine (8.1Å) (Table II).

The access of molecules into zeolite films is not limited to gaseous species. Selectivity is maintained even in aqueous systems. Metal-exchanged zeolite/silica thin films introduce different types of chemical interactions with potential sorbates. For example, pyridine or NH$_3$ diffused into Cu(II)-containing faujasite-silica thin films from aqueous solution coordinate to intrazeolite Cu(II) to form [CuL$_4$]$^{2+}$complexes (Table II). If the pore size of the Cu-zeolite films is reduced below 5Å by incorporating CHA (3.7Å), LTA (4.1Å) or other zeolites in the glassy matrix, pyridine is completely excluded from the pores (Table II). In aqueous phase, the pyridine molecules bind selectively to Cu-FAU films but not to the corresponding Na or NH$_4$ forms.

TABLE II

Remaining intensity of IR spectral peaks after adsorption of probe molecules into modified zeolite-silica thin films.

| Probe | NH$_3$ | pyridine | i-octane | (C$_4$H$_9$)$_3$N | (C$_4$F$_9$)$_3$N |
|---|---|---|---|---|---|
| Kinetic diam./Å | 2.6 | 5.9 | 6.2 | 8.1 | 10.2 |
| Sample | | | | | |
| Gas phase$^a$ | | | | | |
| HY-DC/A2 | | 0% | | | 100% |
| HY-DC/B2 | | 0% | | | 100% |
| H-CHA-SD/A2 | 0% | | | 100% | |
| H-CHA-SD/B2 | 0% | | | 100% | |
| H-ZSM-5 | 0% | | 0% shift$^b$ | 50% | |
| H-ZSM-5-DC/A2 | 0% | 0% | 0% shift | 100% | |
| Aqueous phase$^c$ | | | | | |
| CuY-DC/A2 | | yes | | | |
| CuCHA-SD/A2 | | no | | | |
| CuLTA-SD/A2 | | no | | | |

$^a$Adsorption behavior indicated by the remaining intensities of the 3640 (HY), 3620 (H-CHA) or 3730 cm$^{-1}$ (H-ZSM-5) acidic hydroxyls obtained from the NH$_4$-exchanged forms of the zeolites. Preparation of the zeolite films: DC: Si-wafer dip-coated in zeolite/A2 or B2 suspensions; SD: zeolite dispersion dried on Si-wafer and covered with A2 sol. For sol recipies, see example 1.
$^b$interaction of i-octane with hydroxyls shifts the OH band by about 20 cm$^{-1}$.
$^c$Cu(II)-exchanged zeolites (50% exchanged in 0.1 M Cu(NO$_3$)$_2$) were embedded in the film. Pyridine was equilibrated with these films in water. If the Cu(II) ions react with pyridine, [Cu(py)$_4$]$^{2+}$ is formed, indicated by bands at 1610, 1543, 1487 and 1450 cm$^{-1}$ ('yes').

EXAMPLE 3

Sensor with ZSM-5 zeolite

A glass silica matrix of about 150 nm thickness with embedded crystals of ZSM-5 (pore size 5.4×5.6Å) was coated on the active surface of a SAW device. By passing a stream of dry nitrogen containing organic vapors (0.1% of saturation) over the dried, zeolite-coated SAW device, adsorption into the film results in a frequency response proportional to the adsorbed mass of the sorbate molecules. Indeed, a striking difference in frequency response to different probe molecules is observed (Table III). While vapors of MeOH (about 3.8Å effective diameter) and PrOH (about 4.7Å) adsorb at levels of about 0.5 μg/cm$^2$ in the film, the response to isooctane (6.2Å) is minimal. This dramatic difference can be understood if the effective diameters of these molecules are compared with the pore opening of the zeolite film. The amount of vapor adsorbed in the film corresponds to a density of about 5 μg of accessible ZSM-5 per cm$^2$ of film (assuming saturation of the pores).

TABLE III

Adsorption of organic vapors in H-ZSM-5-DC/A2 film coated on SAW device: pore size 5.3 × 5.6 Å[a].

| Species | Kinetic diam. (Å) | Frequency shift (Hz) | Mass change (ng/cm$^2$) |
|---|---|---|---|
| MeOH | 3.8 | −6,500 | 540 |
| n-PrOH | 4.7 | −10,200 | 840 |
| i-octane[b] | 6.2 | 74 | −6.1 |

[a] vapor 0.1% saturated in N$_2$, measured at 295K, 97 MHz center frequency.
[b] 2,2,4-trimethylpentane. The origin of the observed small negative mass change is probably due to small changes in the elastic properties of the film.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of selectively detecting the presence of a chemical entity within an environment comprising placing a selective chemical sensor in said environment and detecting mass changes of the piezoelectric surface resulting from sorption of material thereon, said chemical sensor comprising:
   (a) a piezoelectric substrate capable of detecting mass changes resulting from sorption of material thereon; and
   (b) a coating applied to said substrate, which selectively sorbs chemical entities of a size less than a preselected magnitude, wherein the chemical entity to be detected is CO or a hydrocarbon,
   wherein element (a) is a surface acoustic wave (SAW) device or a quartz crystal microbalance (QCM) device,
   wherein element (b) is a film containing zeolite crystals, wherein the pores within said zeolite crystals provide molecule sieving capability, and
   wherein said film is an inorganic silica matrix having zeolite crystals embedded therein.

2. A method of selectively detecting the presence of a chemical entity within an environment comprising placing a selective chemical sensor in said environment and detecting mass changes of the piezoelectric surface resulting from sorption of material thereon, said chemical sensor comprising:
   (a) a piezoelectric substrate capable of detecting mass changes resulting from sorption of material thereon; and
   (b) a coating applied to said substrate, which selectively sorbs chemical entities of a size less than a preselected magnitude, wherein the chemical entity to be detected is CO or a hydrocarbon,
   wherein element (a) is a surface acoustic wave (SAW) device or a quartz crystal microbalance (QCM) device,
   wherein element (b) is a film containing zeolite crystals, wherein the pores within said zeolite crystals provide molecule sieving capability,
   wherein said film is an inorganic matrix having zeolite crystals embedded therein, and
   wherein said matrix is selected from the group comprising sol-gel derived glasses, polymers and clay.

3. A chemical sensor comprising:
   (a) a piezoelectric substrate capable of detecting mass changes resulting from sorption of material thereon; and
   (b) a coating applied to said substrate, which selectively sorbs chemical entities of a size less than a pre-selected magnitude, wherein the chemical entity to be detected is CO or a hydrocarbon,
   wherein element (b) is a film containing zeolite crystals, wherein the pores within said zeolite crystals provide molecule sieving capability, and
   wherein said film is an inorganic silica matrix having zeolite crystals embedded therein.

4. A sensor comprising:
   (a) a piezoelectric substrate capable of detecting mass changes resulting from sorption of material thereon; and
   (b) a coating applied to said substrate, which selectively sorbs chemical entities of a size less than a pre-selected magnitude, wherein the chemical entity to be detected is CO or a hydrocarbon,
   wherein element (b) is a film containing zeolite crystals, wherein the pores within said zeolite crystals provide molecule sieving capability,
   wherein said film is selected from the group comprising sol-gel derived glasses, polymers and clays.

5. A sensor comprising:
   (a) a piezoelectric substrate capable of detecting mass changes resulting from sorption of material thereon; and
   (b) a coating applied to said substrate, which selectively sorbs chemical entities of a size less than a pre-selected magnitude, wherein the chemical entity to be detected is CO or a hydrocarbon,
   wherein element (b) is a film containing zeolite crystals, wherein the pores within said zeolite crystals provide molecule sieving capability, and
   wherein the pores of said zeolite crystals are modified so as to be Lewis or Bronsted acidic or basic.

6. A sensor comprising:
   (a) a piezoelectric substrate capable of detecting mass changes resulting from sorption of material thereon; and
   (b) a coating applied to said substrate, which selectively sorbs chemical entities of a size less than a pre-selected magnitude, wherein the chemical entity to be detected is CO or a hydrocarbon,
   wherein element (b) is a film containing zeolite crystals, wherein the pores within said zeolite crystals provide molecule sieving capability, and
   wherein the pores of said zeolite crystals are modified so as to provide intrazeolite ligation by the presence of metal ions.

7. A sensor comprising:
   (a) a piezoelectric substrate capable of detecting mass changes resulting from sorption of material thereon; and
   (b) a coating applied to said substrate, which selectively sorbs chemical entities of a size less than a pre-selected magnitude, wherein the chemical entity to be detected is CO or a hydrocarbon,
   wherein element (b) is a film containing zeolite crystals, wherein the pores within said zeolite crystals provide molecule sieving capability, and wherein said film is an alumina, boro-aluminosilicate, titania, hydrolyzed diethoxydiphenylsilane, or silane rubber matrix containing zeolite crystals.

8. A sensor comprising:
(a) a piezoelectric substrate capable of detecting mass changes resulting from sorption of material thereon; and
(b) a coating applied to said substrate, which selectively sorbs chemical entities of a size less than a pre-selected magnitude, wherein the chemical entity to be detected is CO or a hydrocarbon,
wherein element (b) is a solid, non-porous, inorganic matrix with porous zeolite crystals embedded therein.

9. A selective chemical sensor comprising:
(a) a piezoelectric substrate capable of detecting mass changes resulting from sorption of materials thereon;
(b) a coating applied to said substrate, wherein said coating comprises a solid, non-porous, inorganic matrix and porous zeolite crystals contained within said matrix, wherein the pores of said zeolite crystals selectively sorb chemical entities of a size less than a preselected magnitude.

10. A chemical sensor according to claim 9, wherein said inorganic matrix is a silicon matrix having a thickness of about 0.001–10 microns and said pores of said zeolite crystals have a diameter of about 0.25–1.2 nm.

11. A sensor according to claim 10, wherein said coating is a single layer of zeolite crystals protruding from an amorphous $SiO_2$ matrix.

12. A sensor according to claim 11 wherein element (a) is a surface acoustic wave (SAW) device.

* * * * *